United States Patent [19]

Oswald

[11] 3,998,866
[45] Dec. 21, 1976

[54] THIOETHER PROPYL ISOCYANATES

[75] Inventor: Alexis A. Oswald, Mountainside, N.J.

[73] Assignee: Exxon Research & Engineering Co., Linden, N.J.

[22] Filed: May 9, 1975

[21] Appl. No.: 576,177

Related U.S. Application Data

[60] Continuation-in-part of Ser. No. 107,474, Jan. 18, 1971, Pat. No. 3,884,951, which is a division of Ser. No. 759,200, Sept. 11, 1968, Pat. No. 3,597,341.

[52] U.S. Cl. ..................... 260/453 A; 260/453 AL
[51] Int. Cl.$^2$ ........... C07C 119/042; C07C 119/045
[58] Field of Search ............... 260/453 AL, 453 AR, 260/453 A

[56] References Cited

UNITED STATES PATENTS 3,519,686  7/1970  Nair .............................. 260/453 X

FOREIGN PATENTS OR APPLICATIONS 981,346  1/1965  United Kingdom

OTHER PUBLICATIONS

Siefken: Annalen der Chemie, vol. 562, pp. 114 and 123 (1949).

*Primary Examiner*—Lewis Gotts
*Assistant Examiner*—Dolph H. Torrence
*Attorney, Agent, or Firm*—Robert J. Baran

[57] ABSTRACT

Novel thioether isocyanates and isothiocyanates are produced by the addition of thiols to the olefinic bonds of allyl isocyanates and isothiocyanates. They are useful as pesticides, especially as post-emergence herbicides, and as polymer intermediates.

2 Claims, No Drawings

THIOETHER PROPYL ISOCYANATES

CROSS REFERENCE TO OTHER APPLICATIONS

This application is a continuation-in-part of an application bearing U.S. Ser. No. 107,474, filed on Jan. 18, 1971, now U.S. Pat. No. 3,884,951 which is a division of an application bearing U.S. Serial No. 759,200, filed Sept. 11, 1968, now U.S. Pat. No. 3,597,341 both filed in the name of Alexis A. Oswald.

FIELD OF THE INVENTION

This application relates to alkyl isocyanates having thioether groups. More particularly, this invention relates to the free radical type thiol adducts of allyl isocyanate and isothiocyanate, i.e., 3-substituted thiopropyl isocyanates and isothiocyanates as novel compositions having unexpected properties. These adducts have unexpected utility as active constituents of herbicides and as intermediates in the preparation of polymers of superior stability. One aspect of the application concerns 3-alkylthio or phenylthio substituted propyl isocyanates. Another aspect covers $C_2$ to $C_{20}$ alkylene bis-(thiopropyl isocyanates). A further aspect refers to thiopropyl isocyanate terminated poly-($C_2$ to $C_{20}$ alkylene thioethers). Finally, the application also specifically relates to aliphatic poly-thiopropyl isocyanate compounds.

PRIOR ART

Substituted alkyl isocyanates and isothiocyanates as a general class of compounds are known in the prior art. Some alkyl isocyanates substituted with thioether groups and related compounds were also described.

The most relevant prior art is British Pat. No. 981,346, entitled "Improvements Relating to Polythiomethylene Compounds" and assigned to the DuPont de Nemours and Co. This patent generically discloses polymethylenethioether derivatives of alkyl isocyanates covering thousands of compounds having the divalent —CH$_2$—S— repeating unit. Among the specifically disclosed compounds, the diisocyanate disclosed in Example 12.

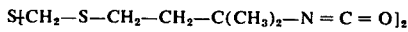

S[CH$_2$—S—CH$_2$—CH$_2$—C(CH$_3$)$_2$—N = C = O]$_2$ is the most closely related to the compounds of the present application. This polymethylene thioether and all the other compounds are polythioformaldehyde compounds, i.e. poly-mercaptals, and as such are thermally unstable at high temperatures and are subject to acid hydrolysis.

Two other patents also disclose specific thioether substituted alkyl isocyanates although only as a part of unrelated shotgun-type disclosures. In U.S. Pat. No. 2,340,757, the inventors, W. Kaase and E. Waltman, disclose a dimercaptal of isocyanatopropionaldehyde.

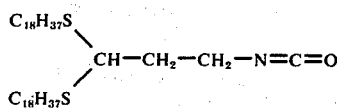

C$_{18}$H$_{37}$S\
       CH—CH$_2$—CH$_2$—N=C=O\
C$_{18}$H$_{37}$S/

This compound as a mercaptal is again acid sensitive. For reference, on the properties of mono-, di- and polymercaptals see Volume XIII, Part III, particularly pages 20 and 28, of the series of monographs on High Polymers, edited by N. G. Gaylord, published by Interscience Publishers, New York, 1962. In another U.S. Pat. No. 3,519,686, by M. D. Nair, a methyl substituted thioethyl isocyanate and isothiocyanate are disclosed. These compounds are of the formula,

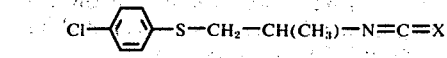

Cl—⟨ ⟩—S—CH$_2$—CH(CH$_3$)—N=C=X wherein X is oxygen or sulfur, and are mentioned as potential intermediates, without property disclosures, for the corresponding amine. 2-Chloroethylthioethyl isocyanates of the formula

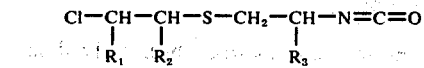

Cl—CH—CH—S—CH$_2$—CH—N=C=O
    |    |            |
    R$_1$  R$_2$           R$_3$ are disclosed by H. Holtschmidt and H. Freytag in U.S. Pat. No. 3,409,631. Neither of the three patents disclose any chemistry which would be applicable to the synthesis of the novel compounds of the present invention.

As a class of compounds, isocyanates are best known as precursors of carbonates or urethanes. Polyurethanes derived from diisocyanates represent an extremely important rapidly growing type of commercial polymers. For a reference on polyurethane chemistry see Volume XVI, Part I, particularly page 13, of the previously referenced series of monographs on High Polymers. This part was written by J. H. Saunders and K. C. Frisch and published by Interscience in 1962. To facilitate further progress in polyurethane chemistry, there is a continuing effort to discover novel di- and polyisocyanate monomers as described in the monograph. "Polyurethane Technology" by P. F. Bruins which was also published by Interscience in New York, 1969.

The alkyl isocyanate compounds of the present invention possess properties absent in the prior art compositions. In general, the present compounds exhibit surprising herbicidal properties and thermal plus oxidative stability. Their stability is especially important in the case of the diisocyanate and polyisocyanate compounds. It allows the use of the latter compounds in the production of novel polyurethanes of exceptional aging and yellowing resistance.

SUMMARY OF THE INVENTION

The anti-Markovnikov adducts of this invention are prepared via the selective free radical addition of selected thiols to certain allylic isocyanates.

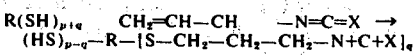

R(SH)$_{p+q}$    CH$_2$=CH—CH    —N=C=X →
(HS)$_{p-q}$—R—[S—CH$_2$—CH$_2$—CH$_2$—N+C+X]$_q$ wherein R is a mono-, di- or polyvalent aromatic or aliphatic hydrocarbon radical including substituted hydrocarbon radicals preferably selected from the group consisting of $C_1$ to to $C_{20}$, preferably $C_1$ to $C_4$ alkyl; $C_2$ to $C_4$ hydroxyalkyl; $C_6$ to $C_{20}$ cycloalkyl; phenyl; chlorinated phenyl; $C_7$ to $C_{20}$ alkylphenyl; $C_7$ to $C_{20}$ phenylalkyl; $C_6$ to $C_{200}$ saturated hydrocarbon radicals interrupted by S in such a manner as to obtain a minimum of two, preferably two or three, adjacent carbon atoms between sulfur atoms; X is oxygen and sulfur, preferably oxygen; p and q are each a positive integer from 1 to 30, preferably 2 to 5, most preferably 3 to 5, with $q$ being equal to or smaller than $p$. The above symbols will be also used to identify more specific compounds in the appropriate context in cases wherein the R hydrocarbon radical has a particular valence rather than a range of valences.

The more preferred isocyanate products of the instant invention have all the thiol groups of the polythiol reacted as shown by the following scheme:

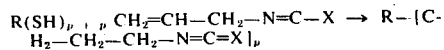

With monothiols the reaction is the following:

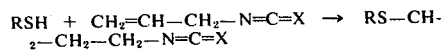

wherein R is a monovalent hydrocarbon radical as defined earlier.

A specifically preferred case is the reaction of a hydroxyalkanethiol with allyl isocyanate

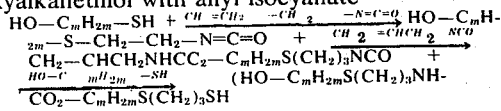

wherein $m$ is 2 to 4 preferably 2 and 3 and the oxygen and sulfur atoms are separated by a minimum of 2 carbon atoms.

Typical, nonlimiting thiol reactants from which the products of the instant invention may be prepared include such thiols as methanethiol, propanethiol, hydroxyethanethiol, alpha-toluenethiol, benzenethiol, xylenethiol, chlorobenzenethiol, t-butanethiol, hexadecanethiol, trichlorobenzenethiol, 3-hydroxypropanethiol, cyclohexanethiol, poly(ethylthio)ethanethiol.

When a dithiol is reacted with an allyl isocyanate or isothiocyanate one or both thiol groups may participate in the addition reaction to the allylic double bond, as is shown in Equation 1 below.

EQUATION 1

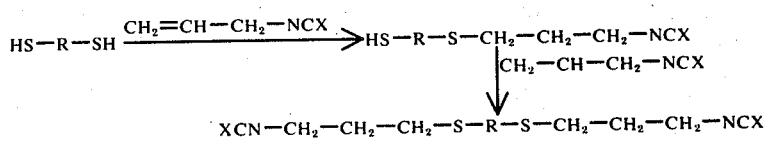

wherein R is a divalent hydrocarbon radical. Preferably R is as described above equal to R' which is $C_2$ to $C_{20}$ alkylene, phenylene, xylylene, $C_6$ to $C_{200}$ alkylene radicals interrupted by S in such a manner as to obtain a minimum of two adjacent carbon atoms between sulfur atoms, X is oxygen and sulfur.

Typical, nonlimiting examples of dithiol reactants include 1,3-propanedithiol, 1,6-hexanedithiol, cyclooctanedithiol, cyclododecanedithiol, 1,2-ethanedithiol, benzenedithiol, xylylene dithiol, 2-thio-bis-ethanethiol, polyethylenethioetherdithiol, polypropylenethioetherdithiol, etc.

The monoadduct intermediate of the dithiol-allyl isocyanate intermediate can undergo a polyselfaddition initiated by heat and/or ionic catalysts to form a polythiourethane, as shown in Equation 2 below.

EQUATION 2

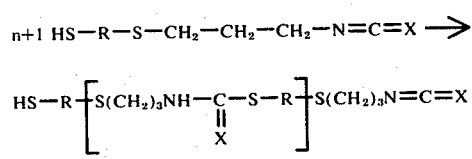

wherein $n$ is 1 to 500, preferably 20 to 200.

Alternatively, the diadduct may be reacted with a diol or dithiol to yield a polyurethane, as shown in Equation 3.

EQUATION 3

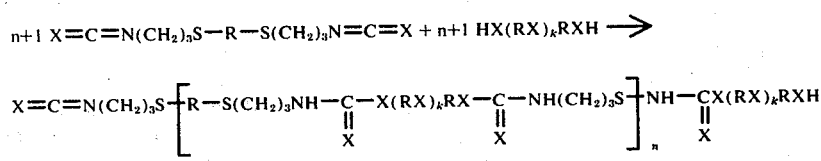

wherein $k$ is 1 to 100 preferably 1 to 30.

In the case of trithiol reactants, the selective additions to allyl isocyanate and isothiocyanate can be carried out to various degrees, as shown in Equation 4.

EQUATION 4

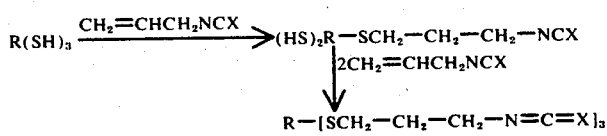

wherein R is a trivalent hydrocarbon radical as described above. Preferably R equals R'' which is the parent trivalent radical hydrocarbon derived from $C_3$ to $C_{20}$ alkanes, $C_6$ to $C_{20}$ cycloalkanes, $C_6$ to $C_{200}$ aliphatic hydrocarbon radicals interrupted by S in such a manner as to obtain a minimum of two, preferably two to three adjacent carbon atoms between sulfur atoms.

In the case of the higher polythiols, i.e. higher than trifunctional, the number of allyl isocyanate molecules reacted per molecule of polythiol can equal up to the number of thiol groups in the polythiol. The general reaction is shown by Equation 5.

EQUATION 5

$$R(SH)_p + q\ CH_2=CHCH_2NCX \rightarrow$$

$$(HS)_{p-q}R(SCH_2CH_2CH_2NCX)_q$$

wherein (1) R is as defined above and (2) $p$ and $q$ are as defined above. Preferably R is R''' which is a polyvalent 6 $C_6$ to $C_{200}$ aliphatic hydrocarbon radical selected from the group consisting of open chain and cyclic unsubstituted radicals and of radicals interrupted with S in such a manner as to obtain a minimum of two adjacent carbon atoms between sulfur atoms.

Typical, preferred nonlimiting examples of trithiol and polythiol reactants include trimercaptoethyl cyclohexane, trimercaptoethylthio cyclododecane, the trimercaptoacetic acid ester of tri-hydroxymethyl methane, the tetra-mercaptopropionic acid ester of pentaerythritol, polypropylenethioether trithiol, the tri-mercaptoacetic ester of pentaerythritol, the polythiol resulting from polybutadiene excess hydrogen sulfide addition, the tetrathiol resulting from trivinyl cyclohexane-hydrogen sulfide addition, the trithiol resulting from polypropylene thioether-dithiol-trivinyl cyclohexane addition, etc.

More preferred dithiols are polymethylene and polyalkylenethioether dithiols, each of which can be reacted with allyl isocyanate in accordance with Equation 6.

EQUATION 6

$$N + 1\ HS+C_mH_{2m}S+_sC_mH_{2m}SH + N+1\ CH_2=CHCH_2NCO \rightarrow ONC(CH_2)_3S+C_mH_2-_mS+_sC_mH_{2m}S(CH_2)_3NHCOS+_n+C_mH_{2m}S]_sC_mH_{2m}SH$$

wherein $m$ is 2 to 4, preferably 2 and 3; $s$ is 0 to 20; and the thioether groups are separated by at least 2 carbon atoms.

A more preferred trithiol is the triaddition product of the reaction of polyalkylene thioether dithiols with trivinyl cyclohexane, preferably the 1,2,4-isomer, which reaction is shown in Equation 7.

EQUATION 7

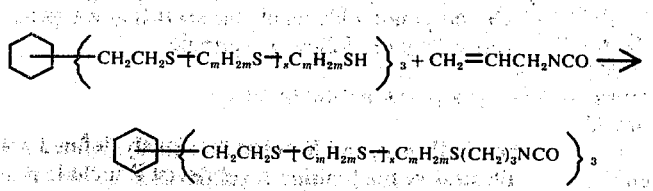

wherein $m$ and $s$ are the same as above.

When allylic isocyanates or isothiocyanates of this invention are reacted with polythiols, it is to be understood that the resulting reaction can be either a partial one or can be run until completion. As an example of a complete reaction of a polythiol the reaction of a preferred type tetrathiol is shown by Equation 8.

EQUATION 8

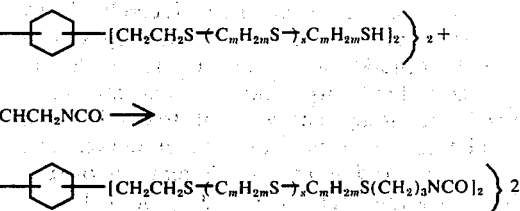

$$4\ CH_2=CHCH_2NCO \rightarrow$$

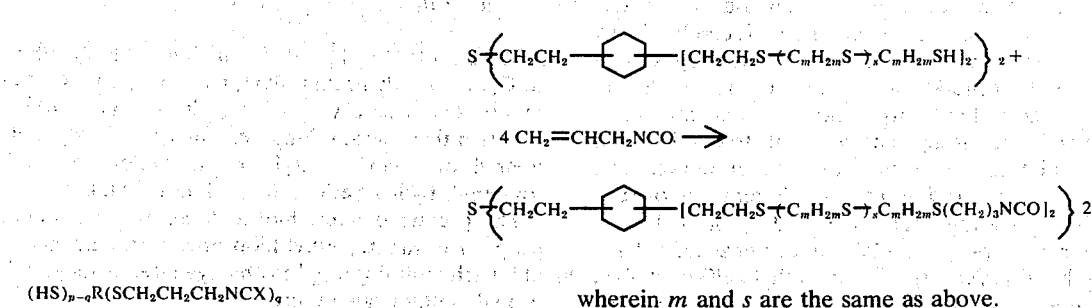

wherein $m$ and $s$ are the same as above.

Without wishing or intending to be bound by any theory, it is nevertheless believed, from the structure of the adducts obtained, that the selective additions of this invention take place by means of a free radical type chain mechanism and in accordance with the following postulated reaction mechanism.

Initiation $$RSH \xrightarrow{radical\ initiator} RS\cdot$$

Propagation

Step (1)

$$RS\cdot + CH_2=CH-CH_2-NCO \rightarrow RS-CH_2-CH-CH_2-NCO$$

Step (2)

$$RS-CH_2-CH-CH_2-NCO + RSH \rightarrow RS-CH_2-CH_2-CH_2-NCO + RS\cdot$$

REACTION CONDITIONS

The reaction temperatures employed in this invention are preferably kept below 100° C., most preferably below about 50° C, in order to avoid concurrent ionic reactions of the isocyanate group which result in the formation of byproducts. The lower limit of the reaction temperature range is defined by the freezing point of the reaction mixture employed, reaction initiation, and the cost of refrigeration. Reaction temperatures are between about −150° and about +100° C, preferably between about −80° and about +50° C. For the initiation of the low temperature, selective free radical reactions, nonchemical initiators are preferred, such as ultraviolet light, gamma radiation, etc. However, chemical initiators can also be used below the temperature limits of the reactions. For example, chemical initiators, such as peroxides, derived from boron alkyls are suitable low temperature initiators. Other chemical initiators include azo compounds, such as bis-azo-ibutyronitrile, etc.

Usually the reactions of this invention are carried out with equivalent amounts of reactants in the liquid phase at atmospheric pressures. If the thiol reactant is gaseous at the reaction temperature, superatmospheric pressure can be used to keep it in the liquid state. Alternatively, such a thiol as, e.g., ethanethiol, can be slowly introduced into the radiated, liquid allylic isocyanate compound. In general, the isocyanate reactants are good solvents for the thiols. Solid thiols can essentially be dissolved in the isocyanate reactants to obtain liquid reaction mixtures. However, the use of nonreactive solvents at times can be desirable. Exemplary of suitable solvents are the open-chain and cyclic hydrocarbons such as heptane, cyclohexane, benzene, xylene, etc.; aliphatic sulfides such as dimethyl sulfide; dialkyl ethers such as diethyl ether; esters such as ethyl acetate; dialkyl sulfones such as diethyl sulfone; etc.

Although the reactants are usually employed in equivalent amounts, an excess of either reactant beyond the stoichiometric requirements can be used with beneficial results. For example, an excess of methanethiol can be used to increase the rate of the overall addition reaction to allyl isocyanates. Upon completion of the free radical addition, the excess thiol can be removed or used for anionic addition to the isocyanate group to form the corresponding thiourethane in accordance with the following equation, Equation 9.

EQUATION 9

  (1)

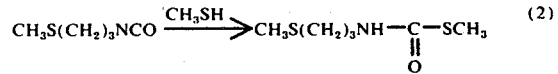  (2)

The dithiol reactants of this invention such as, e.g., ethane dithiol, can be reacted with half of the stoichiometric requirements of allyl isocyanate to yield a thiol isocyanate product which is itself subject to polyautoaddition to thereby result in a polyurethane product in accordance with the following equation, Equation 10.

EQUATION 10

EQUATION 10

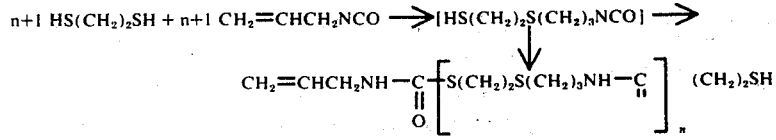

Alternatively, trithiols such as polythioether trithiols can be reacted with an excess of allyl isocyanate to convert them to the corresponding polythioether triisocyanates. The excess allyl isocyanate is then removed by distillation.

In general, the monothiol adducts of this invention are characterized by the formulae:

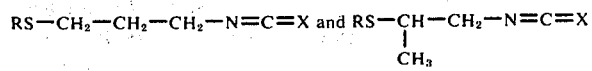

wherein R and X are as previously defined above.

The preferred monothiol adducts of this invention have the formula $RS-CH_2-CH_2-CH_2-N=C=X$ More preferably R is R″″ which is $C_1$ to $C_{20}$ alkyl, $C_1$ to $C_{20}$ monosubstituted alkyl, $C_6$ to $C_{20}$ aryl, $C_6$ to $C_{20}$ monosubstituted aryl, $C_6$ to $C_{20}$ disubstituted aryl.

Illustrative nonlimiting examples of R include methyl, octadecyl, t-butyl, phenyl, cyclohexyl, trichlorophenyl, hydroxyethyl, docosyl, dodecylphenyl.

The preferred monothiol adducts include ethylthiopropyl isocyanate, ethylthiopropyl isothiocyanate, dichlorophenylthiopropyl isothiocyanate, hexadecylthiopropyl isothiocyanate, etc.

In general, the dithiol adducts of this invention are characterized by the following formulae:

and

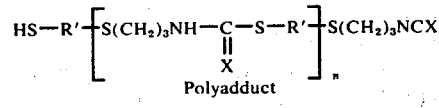

wherein R, X and n are as previously defined above.

Illustrative, nonlimiting examples of R include propylene, trimethylene, ethylene, xylylene, polyethylene/thioether, polypropylenethioether, polydodecamethylenethioether, etc.

In general, the trithiol adducts of this invention are characterized by the following formula:

$R(SCH_2CH_2CH_2NCX)_3$ wherein R is as previously defined above.

Illustrative nonlimiting examples of R include trivalent hydrocarbon radicals derived from cyclododecane, triethylcyclohexane, propane, tris-(ethylthioethyl) cyclohexane. Preferred trithiol adducts are tris-(1,2,4-isocyanatopropylthioethyl) cyclohexane, tris-(1,2,3-isocyanatopropylthio) propane, tris-1,2,3-isocyanatopropylthio-polypropylenethioetherethyl) cyclohexane.

The polythiol adducts of this invention are generally described by the following formula:

$(HS)_{p-q}R(SCH_2CH_2CH_2NCX)_q$ wherein R, p, q, and X are as previously defined above.

Illustrative nonlimiting examples of R include polyvalent hydrocarbon radicals derived from low molecular weight n-paraffins, polypropylene, thio-bis-ethyl (diethyl) cyclohexane. An exemplary polythiol adduct is bis-(diisocyanatopropylthioethyl) cyclohexylethyl thioether.

The anti-Markovnikov adducts of this invention are valuable intermediates which can themselves undergo all the customary reactions undergone by isocyanates and isothiocyanates in general with such typical reactants as alcohols, thiols, acids, amines, oximes, water, etc. Moreover, the products derived from the reaction of dithiols, and polythiols with allylic isocyanates, are especially useful in polymer chemistry as monomers and crosslinking agents. Compared to other aliphatic isocyanates, they are unique in their oxidative aging and thermal stability. In turn, the polyurethanes derived from these monomers also exhibit exceptional stability characteristics.

The hydroxyalkylthiopropyl cyanates can be selfadducted to yield the corresponding polyurethanes, e.g.

n + 1    HO—$C_mH_{2m}S(CH_2)_3NCO$ →
H—[$OC_mH_{2m}S(CH_2)_3NHCO$]$_p$$OC_mH_{2m}S(CH_2)_3$-NCO wherein $p$ is from 1 to 10,000.

The diisocyanate, triisocyanate and polyisocyanate containing adducts of di-, tri- and polythiols are mainly utilized in polymer chemistry as monomer components with diols, triols, polyols and diamines, triamines, polyamines, and water. Their reaction as monomer components leads to polyurethanes and polyureas. Difunctional diisocyanates when reacted with diols and diamines yield linear polymers. Polyfunctional isocyanates are useful as crosslinking agents.

As previously noted, the anti-Markovnikov adducts of this invention are also useful as pesticides, particularly as post-emergence herbicides. For pesticidal uses it is preferable that the adduct be derived from a mono or dithiol. As the other component an allylic isothiocyanate is preferred. It is furthermore preferred that the pesticidal adduct should have a molecular weight of less than 500. The dithiol used in the preparation of pesticides is preferably a $C_2$ to $C_4$ polymethylene dithiol.

When used as post-emergence herbicides, the biologically active ingredients are preferably formulated with a suitable carrier or diluent or combinations thereof.

EXAMPLE 1

Ultraviolet Light-Initiated Addition of Methanethiol to Allyl Isocyanate

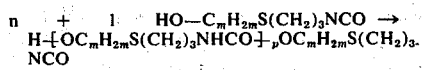

$CH_3SH + CH_2=CHCH_2NCO \longrightarrow CH_3S(CH_2)_3NCO$ (major product)
+ $CH_3SCH(CH_3)CH_2NCO$ (minor product)

Into a quartz pressure tube equipped with a magnetic stirrer and a Teflon screw valve, 49.8 grams (0.6 mole) of allyl isocyanate was placed. Then, 38.4 grams (0.8 mole) of methanethiol was condensed to it, using a dry ice bath. The tube containing the reaction mixture was placed into a water bath, thermostated at 15° C, and mounted upon a magnetic stirrer drive. The stirred reaction mixture was then irradiated from a distance of 5 centimeters by a 75 watt Hanau ultraviolet immersion lamp having a high pressure mercury arc emitting a wide spectrum radiation.

The reaction mixture was sampled during the irradiation to determine the progress of the addition. Nuclear magnetic resonance spectroscopy (nmr) was found to be a suitable, semi-quantitative tool for the analysis of the samples. It showed that 80% of the allyl isocyanate reacted in the first half-hour irradiation time. A total of three hours ultraviolet irradiation resulted in more than 95% conversion of the isocyanate. Nmr also showed that all the addition took place at the olefinic bond. It could also be determined by nmr that 90% of the addition took place in an anti-Markovnikov manner to yield 3-methylthiopropyl isocyanate. About 10% of the adduct was of the opposite orientation, i.e. 2-methylthiopropyl isocyanate. The absence of ionic thiourethane adducts indicated that both adducts were formed by a selective, free radical mechanism.

Distillation of the reaction mixture in vacuo yielded 71.5 grams (91%) of the isomeric adduct mixture as a clear, colorless, mobile liquid, boiling at 33°–35° C at 0.2 mm pressure. A fractional distillation resulted in an enrichment of the branched adduct isomer in the early fractions.

Elemental Analysis — Calculated for $C_5H_9NOS$: C, 45.78; H, 6.91; S, 24.44; N, 10.67. Found: C, 45.52; H, 7.05; S, 24.38; N, 10.66.

EXAMPLE 2

Gamma Irradiation-Initiated Addition of Methanethiol to Allyl Isothiocyanate

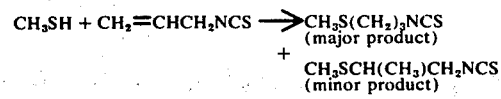

$CH_3SH + CH_2=CHCH_2NCS \longrightarrow CH_3S(CH_2)_3NCS$ (major product)
+ $CH_3SCH(CH_3)CH_2NCS$ (minor product)

A mixture of 69.3 grams (0.7 mole) of distilled allyl isothiocyanate and 32.4 grams (0.675 mole) of methanethiol was reacted in a Pyrex pressure tube under the effect of gamma irradiation. The reaction was initiated from 10 cm distance with 4 $Co^{60}$ plates emitting about 4500 curies. Five hours' irradiation resulted in about 40% conversion of the methanethiol to yield the allylic adducts. About 90% of the isomeric adducts was 3-methylthiopropyl isothiocyanate, while 10% was the branched 2-methylthiopropyl isothiocyanate.

The crude reaction product was distilled in vacuo to yield the isomeric mixture as a clear, light yellow liquid boiling at 76°–78° C at 0.6 mm pressure.

Elemental Analysis — Calculated for the distillate, $C_5H_9NS$: C, 40.78; H, 6.16, S, 43.55. Found: C, 40.38, H, 6.34 and S, 43.57.

A reaction of equimolar amounts of reactants under the above conditions resulted in 53% conversion in 16 hours. The isomeric adduct mixture consisted of about 91% 3-methylthiopropyl isothiocyanate and 9% 2-methylthiopropyl isothiocyanate.

EXAMPLE 3

Ultraviolet Light-Initiated Addition of Methanethiol to Allyl Isothiocyanate

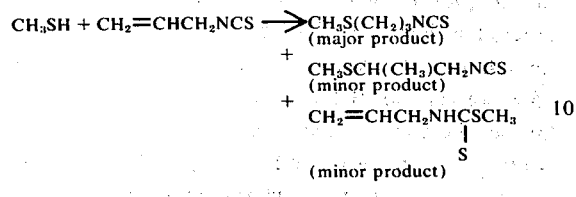

A mixture of 69.3 grams (0.7 mole) of distilled allyl isothiocyanate and 33.6 grams (0.7 mole) of methanethiol was irradiated with two 75 watt Hanau immersion lamps for 127 hours at 16° C, resulting in 90% reaction of the methanethiol. An nmr spectrum of the crude reaction mixture indicated that 80% of the adduct was 3-methylthiopropyl isothiocyanate. Eleven percent was the branched adduct, 2-methylthiopropyl isothiocyanate. About 9% of the adduct was N-allyl-S-methyldithiocarbamate, which resulted by the addition of the thiol to the isothiocyanate group.

Distillation of the crude reaction product in vacuo yielded a mixture of the 3- and 2-methylthiopropyl isothiocyanate as a liquid distillate identical with the product of the previous example.

EXAMPLE 4

Ultraviolet Light-Initiated Addition of 2-Propanethiol to Allyl Isothiocyanate

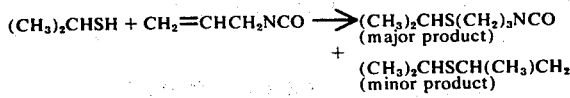

A mixture of 80.7 g (0.97 mole) of distilled allyl isocyanate and 73.9 g (0.97 mole) of 2-propanethiol was irradiated with two Hanau lamps as described in the previous example. Nmr indicated that 5 hours of irradiation resulted in 79%, and 24 hours of total irradiation in 93%, reaction of the allyl isocyanate. After the removal of the unreacted volatile components of the mixture under 0.1 mm pressure, it could be estimated by nmr that the residue consisted of 95% 3-i-propylthiopropyl isocyanate and 5% 2-i-propylthiopropyl isocyanate.

Distillation of the crude residual product at 0.05 mm pressure yielded 140 g of the clear colorless liquid product boiling between 34°–36° C. Based on the reacted amounts of starting materials, this amount corresponds to an isolated yield of 97% for the isomeric mixture of olefinic adducts.

Elemental Analysis — Calculated for $C_7H_{13}CSH$: C, 52.80; H, 8.22; N, 8.79; S, 20.14. Found: C, 52.52; H, 8.28; N, 8.93; S, 19.81.

EXAMPLE 5

Ultraviolet Light-Initiated Addition of 2-Methyl-2-Propanethiol to Allyl Isocyanate

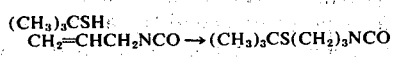

A mixture of 84.2 g (1.01 mole) of distilled allyl isocyanate and 89.3 g (0.99 mole) of 2-methyl-2-propanethiol was irradiated as described in the previous example. Nmr spectroscopy of samples, taken at periodic intervals from the reaction mixture, indicated allyl isocyanate conversions of 64% after 4 hours and of 93% after 64 hours irradiation. After the removal of the volatile reactants in vacuo, nmr analysis of the crude reaction product indicated that it was mostly 3-t-butylthiopropyl isocyanate.

Distillation of the crude product at 0.05 mm yielded 152 g of the clear, colorless liquid boiling between 37°–39° C. This represents a 95% yield based on the converted reactants. Nmr indicates a 95% minimum of the major isomeric adduct.

Elemental Analysis — Calculated for $C_8H_{15}OSN$: C, 55.46; H, 8.72; N, 8.08; S, 18.5. Found: C, 55.31; H, 8.81; N, 8.08; S, 18.48.

EXAMPLE 6

Ultraviolet Light-Initiated Addition of Benzenethiol to Allyl Isocyanate

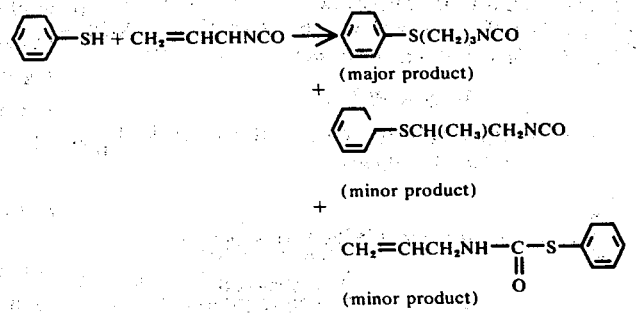

A stirred mixture of 55 grams (0.5 mole) of benzenethiol and 4.36 grams (0.525 mole) of allyl isocyanate was irradiated in a quartz reaction vessel with a 75 watt Hanau immersion lamp at 15° C. Four hours' irradiation resulted in about 50% conversion of the isocyanate as inindicated by nmr. A total of 24 hours irradiation resulted in about 75% conversion of the two isomeric adducts resulting by addition to the olefinic bond. Nmr of the reaction mixture also indicated that the relative percentages of the adducts were 93% 3-phenylthiopropyl isocyanate and 7% 2-phenylthiopropyl isocyanate.

Fractional distillation of the mixture in vacuo yielded 55 grams (57.5%) of the isomeric adducts as a clear, colorless, mobile liquid boiling at 87°–90° C at 0.1 mm. It was observed during distillation that the heating caused some reaction of the thiol with the isocyanate group.

Elemental Analysis — Calculated for $C_{10}H_{11}ONS$: C, 62.15; H, 5.73; N, 7.25; S, 16.59. Found: C, 62.28; H, 5.89; N, 7.19; and S, 16.74.

EXAMPLE 7

Gamma Irradiation-Initiated Addition of Benzenethiol to Allyl Isothiocyanate

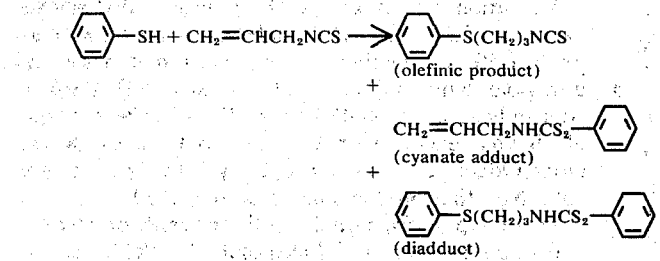

A mixture of 89 grams (0.9 mole) allyl isothiocyanate and 99.25 grams (0.9 mole) benzenethiol was irradiated by gamma rays in the manner described in Example 2. Nmr analysis of a sample after 19 hours irradiation indicated the formation of 19% olefinic adduct. A total of 89 hours irradiation and 120 hours standing without irradiation resulted in the formation of by-products, i.e. diadduct and cyanate adduct as indicated by nmr.

An attempted distillation of the reaction mixture at 0.1 mm pressure from a bath of 135° C. resulted in the decomposition of the by-products according to the following reaction schemes:

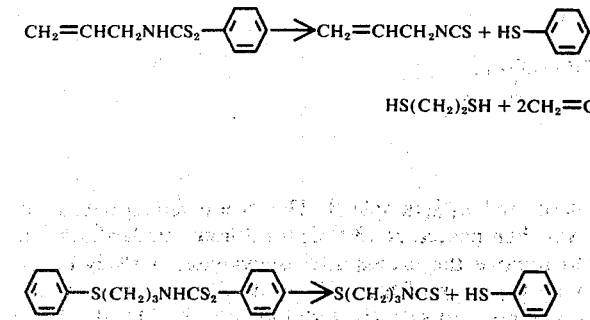

The volatile decomposition products were removed by distillation. Nmr indicated that the residual product (65 g) was mostly the olefinic adduct, i.e., 3-phenylthiopropyl isothiocyanate. Based on the amount of starting materials this corresponds to a yield of 35%.

Elemental Analysis — Calculated for $C_{10}H_{11}S_2N$: C, 57.38; H, 5.29; N, 6.69; S, 30.64. Found: C, 57.11; H, 5.46; N, 7.04; S, 30.45.

EXAMPLE 8

Ultraviolet Light-Initiated Addition of Ethanedithiol to Allyl Isocyanate

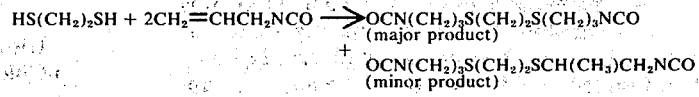

A stirred mixture of 94 grams (1.0 mole) of ethanedithiol at 182.6 grams (2.2 mole) of allyl isocyanate was irradiated in a quartz tube at 15° C. by a 75 watt Hanau ultraviolet immersion lamp. One hour irradiation resulted in the conversion of 55% of the isocyanate. A total of 5 hours irradiation converted about 85% of the isocyanate. Removal of the excess allyl isocyanate by distillation gave a quantitative yield of a crude, residual product having a nmr spectrum corresponding to that of a mixture containing 92% of straight diadduct, ethylene-bis-3-thiopropyl isocyanate, and 8% of the corresponding partially branched diadduct.

Distillation of the crude product in vacuo yielded 161.2 grams (62%) of the diadduct as a colorless, clear liquid, distilling at 147°–150° C. at 0.2 mm pressure. Nmr indicated that the rest of the product, which was a brown residue, also consisted mainly of the same diadduct.

Elemental Analysis — Calculated for $C_{10}H_{16}N_2O_2S_2$: C, 46.13; H, 6.19; N, 10.76; and S, 24.63. Found: C, 46.39; H, 6.32; N, 10.62; and S, 24.56.

EXAMPLE 9

Ultraviolet Light-Initiated Addition of Ethanedithiol to Allyl Isothiocyanate.

$HS(CH_2)_2SH + 2CH_2=CHCH_2NCS \longrightarrow SCN(CH_2)_3S(CH_2)_2S(CH_2)_3NCS$
(olefinic diadduct)
$+ CH_2=CHCH_2NHCS_2(CH_2)_2S_2CNHCH_2CH=CH_2$
(cyanate diadduct)

A mixture of 29.7 grams (0.3 mole) of allyl isothiocyanate and 14.1 grams (0.15 mole) of ethanedithiol was irradiated in the manner described in the previous example. Nmr showed that 120 hours irradiation resulted in the reaction of 45% of the allylic double bonds to form the corresponding allylic adducts. About 22% of the thiocyanate groups also reacted to form the cyanate adducts.

EXAMPLE 10

Gamma Irradiation-Initiated Addition of Ethanedithiol to Allyl Isothiocyanate

A mixture of 99 grams (1 mole) of allyl isothiocyanate and 47 grams (0.5 mole) of ethanedithiol was reacted with initiation from a gamma ray source as described in Example 2. Nmr indicated that 22 hours radiation resulted in 32% reaction of the allylic group.

Subsequent irradiation for 70 hours plus 8 days standing resulted in a final reaction mixture, in which 57% of the allylic and 18% of the isocyanate double bonds were reacted.

An attempted distillation of the reaction mixture from a bath at 135° C at 0.2 mm pressure resulted in the decomposition of the dithiocarbamate groups formed by isothiocyanate addition. For example, the decomposition of the isothiocyanate diadduct can be indicated by the following scheme:

CH$_2$=CHCH$_2$NHCS$_2$CH$_2$CH$_2$S$_2$CNHCH$_2$CH=C-H$_2$ → 2 CH$_2$=CH$_2$NCS + HSCH$_2$CH$_2$SH

The volatile decomposition products were removed by distillation. An nmr spectrum of the residual product (120 g) indicated that it was mostly the olefinic diadduct, i.e. 3-(ethylene)-bis-thiopropyl isothiocyanate. Based on the amount of starting materials, the residual adduct was obtained in a yield of 82%.

EXAMPLE 11

Ultraviolet Light-Initiated Addition of Ethyl Mercaptoacetate to Allyl Isocyanate

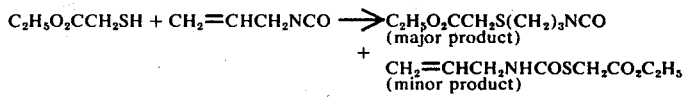

A mixture of 83 grams (1 mole) of allyl isocyanate and 120 grams (1 mole) of ethyl mercaptoacetate was irradiated by two ultraviolet lamps as described in Example 1. Nmr analysis showed that most of the thiol reacted in an hour. About 75% thiol addition occured to the allylic double bond. To complete the reaction, the reaction mixture was irradiated for 14 more hours. The volatile components of the mixture were then removed at 0.05 mm. As a residual product, 190 grams (93%) of crude adduct was obtained. Nmr indicated that it contained 80% of the major product, i.e. i.e. 3-carboethoxymethylthiopropyl isocyanate and about 15% of the minor product, i.e. ethyl S-(N-allyl)-carbamoyl thiolacetate.

An attempted distillation of the crude adduct yielded some 3-carboethoxymethylthiopropyl, isocyanate, as a clear colorless liquid distilling at 97° C. under 0.5 mm pressure with decomposition.

Elemental Analysis — Calculated for C$_8$H$_{13}$NO$_3$S: C, 47.28 H, 6.44; N, 6.89; S, 15.77. Found: C, 47.05; H, 6.46; N, 6.75; S, 15.63

EXAMPLE 12

Ultraviolet Light-Initiated Addition of p-Chlorobenzenethiol to Allyl Isocyanate

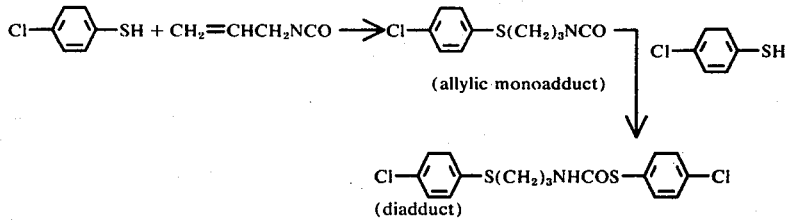

A solution of 41.5 grams (0.5 mole) of allyl isocyanate and 72.25 grams (0.5 mole) of p-chlorobenzenethiol in 50 ml dimethyl sulfide was irradiated with an ultraviolet lamp in the manner described in Example 1. Nmr indicated that in 48 hours 32% of the allylic double bonds reacted with the thiol to form the allylic monoadduct, i.e. 3-p-chlorophenylthiopropyl isocyanate. No other products could be observed.

An attempt to fractionally distill the reaction mixture at 0.1 mm from a 160° C. bath resulted in the formation of the diadduct as a residual product.

EXAMPLE 13

Gamma Irradiation-Initiated Addition of Polythioether Dithiol to Allyl Isocyanate

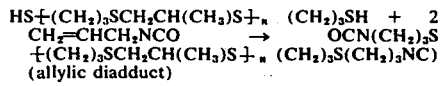

A magnetically stirred mixture of 20 grams (0.24 mole) of allyl isocyanate and 110 grams (0.1 mole) of polythioether (PTE) dithiol of the above formula was irradiated with gamma rays for 16 hours in the manner described in Example 3. The crude reaction product was then heated at 130° C. for 2 hours under 0.05 mm to remove the excess allyl isocyanate. A study of the nmr spectrum of the residual product indicated that a complete and selective addition of the PTE dithiol to form the allylic diadduct took place. A number average molecular weight determination of the product in benzene solution by a vapor pressure osmometer gave a value of 1268. The calculated molecular weight of the diadduct is 1266.

Elemental Analysis — Calculated for C$_{47}$H$_9$N$_2$O$_2$S$_{14}$ (diadduct) of 1168 molecular weight): C, 48.33; H, 8.12; N, 2.39; S, 38.43; Found: C, 48.13; H, 8.02; N, 2.40; S, 38.90.

EXAMPLE 14

Ultraviolet Light-Catalyzed Addition of Allyl Isocyanate to Polythioether Tetrathiol

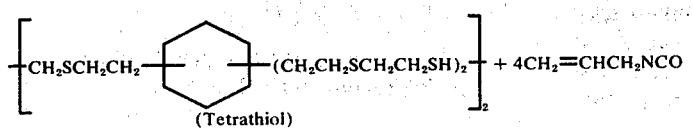

(Tetrathiol)

Molecular Weight Calculated 795.5
Found 897
Number of SH Groups per Molecule Calculated 4.0
Found 4.4

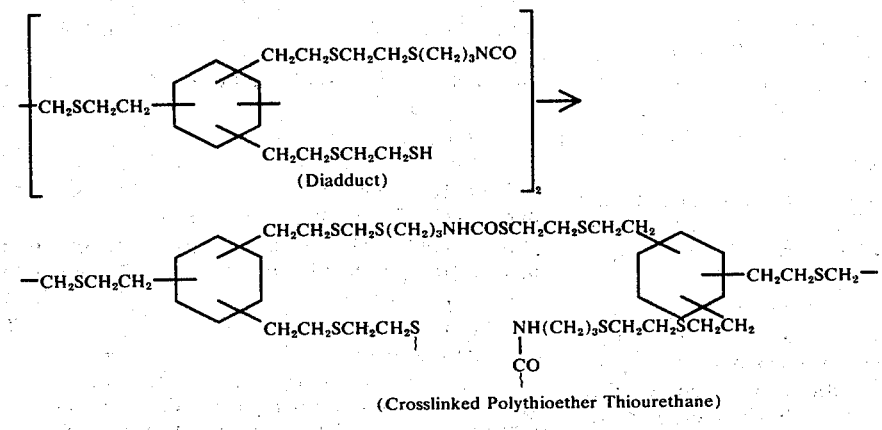

(Crosslinked Polythioether Thiourethane)

A magnetically stirred mixture of 32.12 grams (0.39 mole) of allyl isocyanate and 80.7 grams (0.09 mole) of liquid polythioether (PTE) tetrathiol, derived from the addition of ethanedithiol to 1,2-4-trivinyl cyclohexane, was irradiated with an ultraviolet lamp in the manner described in Example 3. The progress of the allylic addition reaction was followed by nmr spectroscopy. In 28 hours, 69% of the allyl isocyanate reacted. A liquid product mixture consisting of a major amount of triadduct and a minor amount of diadduct was formed. The unreacted allyl isocyanate was removed from this mixture at 0.2 mm at room temperature. Subsequent heating of the liquid residual product at 135° C for two hours resulted in crosslinking. This is due to a thermally induced ionic reaction of the thiol groups with the isocyanate groups to form thiourethane bonds. The crosslinked product is a very tough, hard polymer insoluble in benzene.

EXAMPLE 15

Ultraviolet Light-Initiated Addition of βHydroxyethanethiol to Allyl Isocyanate $HOCH_2CH_2SH + CH_2=CHCH_2NCO \longrightarrow HOCH_2CH_2S(CH_2)_3NCO$
(allylic monoadduct)

$\longrightarrow HOCH_2CH_2S[(CH_2)_3NHCO_2CH_2CH_2S]_n(CH_2)_3NCO$
(polythioether polyurethane polyadduct)

A mixture of 91.3 grams (1.1 mole) of allyl isocyanate and 78 grams (1 mole) of hydroxyethanethiol was irradiated with an ultraviolet lamp in the manner described in Example 1 for 100 minutes. Nmr spectroscopy indicated that allylic monoaddition took place with a reactant conversion of 95%. The unreacted volatile components of the mixture were removed under diffusion pump vacuum at $1.5 \times 10^{-3}$ mm. The resulting residual product is 3-βhydroxyethylthiopropyl isocyanate, a clear, colorless, mobile liquid. During 72 hours standing at room temperature, it was converted into a linear polythioether polythiourethane of 7589 number average molecular weight by self-polyaddition.

Elemental Analysis — Calculated for $C_6H_{11}NOS$: C, 49.63; H, 7.63; N, 9.64; S, 22.08. Found: C, 49.75; H, 7.48; N, 8.78; S, 21.68.

EXAMPLE 16

Ionic Addition of Thiolacetic Acid to Allyl Isocyanate

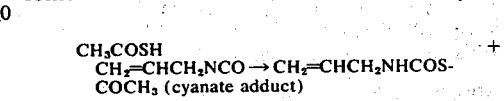

To 43.6 grams (0.525 mole) of stirred allyl isocyanate 38 grams (0.5 mole) of thiolacetic acid was added dropwise below 33° C. in 15 minutes. An exothermic reaction started immediately with the addition of the acid, which required icewater cooling during the addition. The excess allyl isocyanate was subsequently removed at 0.25 mm overnight. The nmr spectrum of the liquid, residual product showed that a quantitative yield of the ionic adduct derived by addition to the isocyanate group was obtained.

EXAMPLE 17

Ultraviolet Light-Catalyzed Addition of n-Dodecanethiol to Allyl Isocyanate

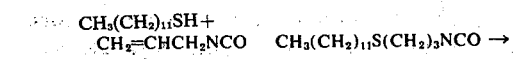

A mixture of 16.6 grams (0.2 mole) of allyl isocyanate and 40.4 grams (0.2 mole) of n-dodecanethiol is irradiated by an ultraviolet lamp in the manner described in Example 1 for 24 hours. An nmr spectrum of the resulting reaction product shows that it is mostly the straight chain olefinic adduct, i.e. 3-n-dodecyl thiopropyl isocyanate.

EXAMPLE 18

Ultraviolet Light-Catalyzed Addition of Ethanethiol to Allyl Isocyanate

$C_2H_5SH + CH_2=CHCH_2NCO \rightarrow C_2H_5S(CH_2)_3NCO$
(olefinic adduct)

A mixture of 16.6 grams (0.2 mole) of allyl isocyanate and 12.4 grams (0.2 mole) of ethanethiol is irradiated at −30° C for 24 hours in the manner described in Example 1 to yield the olefinic adduct, i.e. 3-ethylthiopropyl isocyanate as the major product.

EXAMPLE 19

Ultraviolet Light-Catalyzed Addition of Xylenethiol to 2-Methallyl Isocyanate

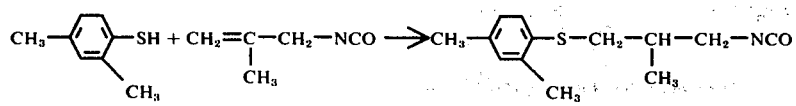

A mixture of 27.6 grams (0.2 mole of xylenethiol and 16.6 grams (0.2 mole) of 2-methallyl isocyanate is irradiated as described in Example 1 for 24 hours. An examination of the reaction mixture by nmr shows that the methallylic adduct, i.e. 3-xylylthiopropyl isocyanate, is formed.

EXAMPLE 20

Azo-bis-Isobutyronitrile Catalyzed Addition of Methanethiol to Allyl Isothiocyanate A magnetically stirred mixture of 29.7 grams (0.3 mole) of allyl isothiocyanate, 15.4 grams (0.31 mole) of methanethiol and 3.3 grams (0.02 mole) of azo-bis-isobutyronitrile was heated for 24 hours at 40° C. A subsequent examination of the reaxtion mixture showed that a free radical addition to form 3-methylthiopropyl isocyanate occurred with 30% conversion. In 96 hours the conversion was 70%.

EXAMPLE 21

Thiol-Allylic Isocyanate and Isothiocyanate Adducts as Post-Emergence Herbicides A number of the adducts from those prepared in the previous examples were evaluated for post-emergence herbicidal activity in this example. The test procedure employed was as follows:

Appropriate crop plant and weed species were seeded by growth-time requirement schedules in individual disposable four-inch square containers, watered as required, and maintained under greenhouse conditions. When all crop plants and weeds had reached suitable growth development, generally first true leaf stage, plants and weeds appropriate to pertaining test requirements were selected for uniformity of growth and development. One four-inch container of each plant and weed, averaging six (Corn) to 50 (Crabgrass) or more plants or weeds per individual container, was then placed on carrying tray for treatment. Generally, six crop and six weed containers were used in each evaluation.

Candidate compounds were dissolved in acetone and, as appropriate, diluted in water containing wetting and emulsifying agents. Although isocyanates can react with water the results were not significantly influenced when, instead of the acetone solutions, aqueous emulsions were used for spraying the containers.

The application rate was ten pounds per acre and, as "controls", allyl isocyanate and the sodium salt of 2,4-dichlorophenoxy acetic acid were used at the 10- and 2-pounds per acre rate, respectively. The results are given in Table I below, and show that the adducts of this invention are effective post-emergence herbicides. While not wishing or intending to be bound by any theory, it is, nevertheless, believed that, or acceptable biological activity, the presence of both the thioether and the isocyanate groups is necessary; allyl isocyanate shows little activity. It is to be further noted that the isothiocyanate adduct of the methanethiol is more active than the corresponding isocyanate adduct and that the aromatic thioether isocyanates seem to be preferable to the corresponding aliphatic thioethers.

TABLE I

POSTEMERGENCE HERBICIDAL ACTIVITY OF ISOCYANATES AND ISOTHIOCYANATES
Physiological Response of Plants

| Example No. | Chemical Structure | Rate Lbs/Acre | Injury to Crops — Sugar Beets | Corn | Oats | Clover | Soy Beans | Injury to Weeds — Cotton | Mustard | Yellow Foxtail | Barnyard Grass | Crab Grass | Buckwheat | Morning Glory | Overall Response — Crop Index | Weed Index |
|---|---|---|---|---|---|---|---|---|---|---|---|---|---|---|---|---|
| 1 | CH$_3$SCH$_2$CH$_2$-CH$_2$NCS | 10 | 8 C | 6 C | 3 C | 10 C | 9 C | 10 C | 9 C | 10 C | 10 C | 10 C | 3 C | 10 C | 7.6 | 8.6 |
| 2 | CH$_3$SCH$_2$CH$_2$-CH$_2$NCO | 10 | 5 C | 3 C | 3 C | 9 C | 9 C | 8 C | 7 C | 6 C | 5 C | 10 C | 6 C | 5 C | 6.1 | 6.5 |
| 6 | ⟨phenyl⟩-SCH$_2$CH$_2$-CH$_2$NCO | 10 | 9 C | 7 C | 7 C | 10 C | 9 C | 10 C | 10 C | 10 C | 10 C | 10 C | 10 C | 10 C | 8.6 | 10.0 |
| 8 | +CH$_3$SCH$_2$-CH$_2$CH$_2$-NCO]$_2$ | 10 | 0 — | 6 C | 7 C | 6 C | 6 C | 4 C | 9 C | 10 C | 8 C | 10 C | 10 C | 8 C | 4.8 | 9.1 |
| Con- | CH$_2$=CH- | 10 | 2 C | 0 — | 0 — | 3 — | 5 — | 0 — | 3 C | 2 C | 3 C | 5 C | 0 — | 0 — | 1.6 | 2.1 |

TABLE I-continued

POSTEMERGENCE HERBICIDAL ACTIVITY OF ISOCYANATES AND ISOTHIOCYANATES
Physiological Response of Plants

| Example No. | Chemical Structure | Rate Lbs/Acre | Injury to Crops[a] | | | | | | Injury to Weeds[a] | | | | | | Overall Response[a] | |
|---|---|---|---|---|---|---|---|---|---|---|---|---|---|---|---|---|
| | | | Sugar Beets | Corn | Oats | Clover | Soy Beans | Cotton | Mustard | Yellow Foxtail | Barnyard Grass | Crab Grass | Buckwheat | Morning Glory | Crop Index | Weed Index |
| trol | $CH_2NCO$ | | | | | | | | | | | | | | | |
| Control | 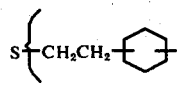  —$OCH_2CO_2$-Na | 2 | 10 D | 0 — | 0 — | 10 D | 8 D | 9 C | 10 C | 0 — | 0 — | 0 — | 10 D | 10 D | 6.1 | 5.0 |

[a]0: No visible effect. 1–3: Slight injury; plant usually recovered with little or no reduction in top growth. 4–6: Moderate injury; plants usually recovered but with reduced top growth. 7–9: Severe injury; plants usually did not recover. 10: All plants killed. C: Caustic. D: Distorted.

EXAMPLE 22

Pesticidal Spectrum of 3-Methylthiopropyl Isothiocyanate

3-Methylthiopropyl isothiocyanate, the product of Example 2, was examined in various standard pesticidal screening tests for its pesticidal activity.

An aqueous emulsion containing 0.05% of the active chemical was found to kill, as a systemic poison, pea aphids.

When applied as an acetone solution at a rate of 100 lbs. active material per four-inch deep acre, the chemical completely controlled the root knot nematode on tomatoes.

When tested as a foliar fungicide on 6–8 inch high wheat plants, an acetone solution containing 0.5% of the chemical completely protected the plants against the cereal leaf rust, Puccinia recondita.

As a soil fungicide, the chemical was active against Rhizoctonia from cotton and Fusarium from tomato. For a positive effect, the compound was applied as an acetone solution at a rate of 36 lbs. per acre active material to the soil.

It should be understood from the foregoing that the above description is merely illustrative of the preferred embodiments and specific examples of the present invention and that in all of which embodiments and examples, variations, such as, e.g. those previously described, can be made by those skilled in the art without departing from the spirit and purview thereof, the invention being defined by the following claims.

What is claimed is:

1. Triisocyanate compounds of the formula $$R''-[SCH_2-CH_2-CH_2-N=C=O]_3$$

wherein $R''$ is a trivalent hydrocarbon radical selected from the group consisting of $C_3$ to $C_{20}$ alkanes, $C_6$ to $C_7$ cycloalkanes, $C_6$ to $C_{200}$ aliphatic hydrocarbon radicals interrupted by S in such a manner as to obtain a minimum of two adjacent carbon atoms between sulfur atoms.

2. Tetraisocyanate compounds of the formula

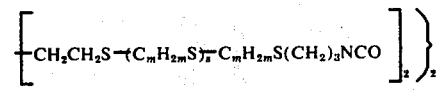

wherein $m$ is 2 to 4; $s$ is 0 to 20 and the thioether groups are separated by at least 2 carbon atoms.